United States Patent
Kim et al.

(10) Patent No.: US 11,879,138 B2
(45) Date of Patent: Jan. 23, 2024

(54) METHOD FOR PREPARING MESENCHYMAL STEM CELL-DERIVED EXOSOMES AND CULTURE SOLUTION PRODUCED FROM THE SAME

(71) Applicant: CK-EXOGENE CO., LTD., Seoul (KR)

(72) Inventors: Jae Young Kim, Gyeonggi-do (KR); Yong Joon Chwae, Gyeonggi-do (KR)

(73) Assignee: CK-EXOGENE CO., LTD., Seoul (KR)

( * ) Notice: Subject to any disclaimer, the term of this patent is extended or adjusted under 35 U.S.C. 154(b) by 32 days.

(21) Appl. No.: 17/434,117

(22) PCT Filed: Jun. 29, 2020

(86) PCT No.: PCT/KR2020/008450
§ 371 (c)(1),
(2) Date: Aug. 26, 2021

(87) PCT Pub. No.: WO2021/241798
PCT Pub. Date: Dec. 2, 2021

(65) Prior Publication Data
US 2022/0348881 A1    Nov. 3, 2022

(30) Foreign Application Priority Data

May 25, 2020   (KR) .................. 10-2020-0062365

(51) Int. Cl.
*C12N 5/0775*      (2010.01)
*A61K 8/14*        (2006.01)
*A61K 35/28*       (2015.01)

(52) U.S. Cl.
CPC .............. *C12N 5/0667* (2013.01); *A61K 8/14* (2013.01); *A61K 35/28* (2013.01); *A61K 2800/10* (2013.01)

(58) Field of Classification Search
None
See application file for complete search history.

(56) References Cited

U.S. PATENT DOCUMENTS

2015/0190430 A1* 7/2015 Lim .................. A61P 17/02
                                          424/489
2017/0073659 A1* 3/2017 Kim ................. G01N 33/57484

FOREIGN PATENT DOCUMENTS

| JP | 2015-523058 A | 8/2015 |
| KR | 10-2018-0131158 A | 12/2018 |
| KR | 10-2019-0028677 A | 3/2019 |
| KR | 10-1985941 B1 | 6/2019 |
| KR | 10-2184428 B1 | 11/2020 |
| WO | WO-2017/152035 A1 | 9/2017 |

OTHER PUBLICATIONS

Office Action from corresponding Indian Patent Application No. 202217025138, dated May 15, 2022.
Office Action from corresponding Japanese Patent Application No. 2021-563388, dated Jan. 31, 2020.
Office Action from corresponding Japanese Patent Application No. 2021-563388, dated Jun. 28, 2020.
Liu, Z., et al.; "TNF-α Induced the Enhanced Apoptosis of Mesenchymal Stem Cells in Ankylosing Spondylitis by Overexpressing Trail-R2", Hindawi, Stem Cells International, vol. 2017, Article ID 4521324, 14 pages.
Yang, R., et al.; "Autophagy Plays a Proective Role in Tumor Necrosis Factor-α-Induced Apoptosis of Bone Marrow-Derived Mesenchymal Stem Cells", Stem Cells and Development, vol. 25, No. 10, 2018, pp. 788-797.
Pöllänen, T. N., et al.; "Exosomal secretion of death bullets: a new way of apoptopic escape?" Am J Physiol Endocrinol Metab, 303, E1015-1024, 2012.
Office Action from corresponding Russian Patent Application No. 2022111154, dated Dec. 5, 2022.
Search Report from corresponding Russian Patent Application No. 2022111154, dated Dec. 5, 2022.
Office Action from corresponding Chinese Patent Application No. 202080032199.X, dated May 27, 2022.
Office Action from corresponding Japanese Application No. 2021-563388, dated Jun. 22, 2023.

\* cited by examiner

*Primary Examiner* — Blaine Lankford
(74) *Attorney, Agent, or Firm* — Harness, Dickey & Pierce, P.L.C.

(57) ABSTRACT

The present application provides a method for preparing mesenchymal stem cell-derived exosomes, the method including: obtaining a cell sample from mesenchymal stem cells and sub-culturing the cell sample, culturing the sub-cultured cells in a substrate medium containing a protein synthesis inhibitory enzyme, and then obtaining a cell culture solution, and isolating exosomes from the cell culture solution, and a cell culture solution produced therefrom. The method for preparing exosomes of the present application has an advantage in that high purity and high concentration exosomes can be isolated.

9 Claims, 8 Drawing Sheets

METHOD FOR PREPARING MESENCHYMAL STEM CELL-DERIVED EXOSOMES AND CULTURE SOLUTION PRODUCED FROM THE SAME

CROSS-REFERENCE TO RELATED APPLICATIONS

This application is a national phase application of PCT Application No. PCT/KR2020/008450, filed on Jun. 29, 2020, which claims the benefit and priority to Korean Patent Application No. 10-2020-0062365, filed on May 25, 2020. The entire disclosures of the applications identified in this paragraph are incorporated herein by references.

TECHNICAL FIELD

This application claims priority to and the benefit of Korean Patent Application No. 10-2020-0062365 filed in the Korean Intellectual Property Office on May 25, 2020, the entire contents of which are incorporated herein by reference.

The present application relates to a method for preparing mesenchymal stem cell-derived exosomes.

BACKGROUND ART

It has been found that there are several types of progenitors in human bone marrow, and among them, progenitors exhibiting multipotency are called mesenchymal stem cells (MSCs). Mesenchymal stem cells are known to be present not only in bone marrow, but also in most organs of the body, such as fat, the liver, and muscle.

It is known that mesenchymal stem cells have the ability to self-proliferate, can differentiate into osteoblasts, chondrocytes, myocytes, marrow stromal cells, tendon-ligament fibroblasts, adipocytes, and the like, and have anti-inflammatory and immunomodulatory ability as highly proliferative adherent cells. In particular, mesenchymal stem cells exhibit imunosuppressive effects such as inhibition of proliferation and differentiation of T cells and B cells and inhibition of functions of immune cells such as dendritic cells, natural killer (NK) cells, and macrophages.

These mesenchymal stem cells have drawn attention because various factors (paracrine/secretory factors) which mesenchymal stem cells secrete, for example, chemokines, cytokines, growth factors, and the like represent the effects of stem cells rather than the differentiation functions of mesenchymal stem cells themselves. Further, mesenchymal stem cells are known to secrete not only these factors, but also extracellular vesicles (EVs), and extracellular vesicles are known to affect various aspects such as the fate, function, and differentiation of cells through intercellular signal transduction.

Among various factors, an exosome is a vesicle consisting of a lipid bilayer, and is a constituent of materials which cells secrete extracellularly. It is known that the exosome serves to transport (convey) a protein, a bioactive lipid and RNA (miRNA), which are intracellular biomolecules, in order to perform a functional role of mediating cell-cell communication and cellular immunity. These exosomes have been studied as biomarkers for neurological diseases such as Alzheimer's disease, and have also been used to develop a drug delivery system such as a nanocarrier of a specific drug due to having selective permeability high enough to permeate the blood-brain barrier (BBB) that separates cerebrospinal fluid and blood.

Meanwhile, it is known that exosomes secreted from mesenchymal stem cells are involved in cell-to-cell communication and exhibit regenerative medicine therapeutic efficacy that stem cells have, and recently, studies on therapeutic effects for various diseases using exosomes secreted by mesenchymal stem cells without using mesenchymal stem cells themselves have been actively conducted.

However, ultracentrifugation most commonly used among exosome isolation methods has an advantage in that a large amount of exosomes can be isolated at one time, but has problems in that expensive equipment is required, it takes a lot of time to isolate exosomes, physical damage may occur to exosomes due to strong centrifugation, and particularly, the purity of isolated exosomes is decreased, and the like. Among methods for alleviating these problems, there is a PS affinity method which increases the purity of exosomes isolated using a material which specifically binds to phosphatidylserine (PS) which is a protein present in the membrane of exosomes, but while the method can isolate high purity exosomes compared to the ultracentrifugation method, there is a disadvantage in that the yield is low. In addition, a method for obtaining exosomes using column chromatography has been reported in the related art, but has a problem in that lipoproteins having size and density similar to those of exosomes suspended in a cell culture solution or blood are eluted together.

Therefore, there is a need for developing an isolation method capable of obtaining high purity exosomes at high concentration from mesenchymal stem cells without impurities.

SUMMARY

Technical Problem

A preparation method according to an exemplary embodiment of the present application has been devised to solve the aforementioned problems in the related art, and is for extracting exosomes at high purity and high concentration from mesenchymal stem cells without impurities.

The present application has been made in an effort to provide a method for preparing mesenchymal stem cell-derived exosomes.

The present application has been made in an effort to provide a culture solution including mesenchymal stem cell-derived exosomes produced using the preparation method.

The present application has been made in an effort to provide a pharmaceutical composition including exosomes produced using the preparation method as an active ingredient.

The present application has been made in an effort to provide a cosmetic composition including exosomes produced using the preparation method as an active ingredient.

Technical Solution

To solve the above-described problems, an exemplary embodiment of the present application provides a method for preparing mesenchymal stem cell-derived exosomes, the method including: obtaining a cell sample from mesenchymal stem cells; sub-culturing the cell sample in a low-glucose Dulbecco's Modified Eagle's Medium (DMEM) medium; culturing the sub-cultured cells in a substrate medium containing a protein synthesis inhibitory enzyme, and then obtaining a cell culture solution; and isolating exosomes from the cell culture solution.

In an exemplary embodiment of the present application, in the obtaining of the stem cell culture solution, the substrate medium may further include TNFα.

In an exemplary embodiment of the present application, TNFα may be included at a concentration of 5 to 500 ng/mL.

In an exemplary embodiment of the present application, the protein synthesis inhibitory enzyme may be any one or two or more selected from the group consisting of cycloheximide, anisomycin, aurintricarboxylic acid, diphtheria toxin, edeine, fusidic acid, pactamycin, puromycin), ricin, sodium fluoride, sparsomycin, tetracycline, and *trichoderma*.

In an exemplary embodiment of the present application, the substrate medium may have a TNFα:protein synthesis inhibitory enzyme ratio of 1:10 to 1:2000.

In an exemplary embodiment of the present application, a treatment time of the TNFα and the protein synthesis inhibitory enzyme may be 30 to 100 hours.

In an exemplary embodiment of the present application, in the cell culture solution, the number of exosomes and a content of any one or more of an exosome-derived protein and exosome-derived RNA may be increased.

In an exemplary embodiment of the present application, $1.1 \times 10^{11}$ or more exosomes per ml of the cell culture solution may be isolated.

In an exemplary embodiment of the present application, in the sub-culturing of the cell sample, the medium may include one or more selected from the group consisting of EGF, FGF-2, GDF11, KGF, HGF, PDGF, VEGF, IGF, and TGF-b.

In an exemplary embodiment of the present application, the sub-culturing of the cell sample may be performed for 4 to 10 passages.

In an exemplary embodiment of the present application, the marker for exosomes may be one or more selected from the group consisting of CD63, CD9, CD81, S1PR1, and S1PR3.

In an exemplary embodiment of the present application, in the obtaining of the sample, the mesenchymal stem cells may be obtained from adipose tissue or placental tissue.

In an exemplary embodiment of the present application, the stem cell may be an embryonic stem cell, an adult stem cell, or an induced pluripotent stem cell (IPS).

An exemplary embodiment of the present application provides a culture solution including mesenchymal stem cell-derived exosomes prepared using the method.

An exemplary embodiment of the present application provides a pharmaceutical composition including mesenchymal stem cell-derived exosomes produced using the method as an active ingredient.

An exemplary embodiment of the present application provides a cosmetic composition including mesenchymal stem cell-derived exosomes produced using the method as an active ingredient.

Advantageous Effects

A method for preparing mesenchymal stem cell-derived exosomes according to an exemplary embodiment of the present application has an advantage in that high purity exosomes can be obtained at a high yield.

The method for preparing mesenchymal stem cell-derived exosomes according to an exemplary embodiment of the present application has an advantage in that a large amount of exosomes can be isolated by treating a substrate medium with TNFα and/or a protein synthesis inhibitory enzyme.

A culture solution including the mesenchymal stem cell-derived exosomes according to an exemplary embodiment of the present application has an advantage in that differentiation ability and proliferation ability are enhanced.

There is an advantage in that it is possible to provide a pharmaceutical composition or cosmetic composition using a culture solution according to an exemplary embodiment of the present application, and the pharmaceutical composition has an advantage in that the probability that side effects against a drug occur can be reduced due to a characteristic that exosomes are cell-free.

DETAILED DESCRIPTION

Figure 1:
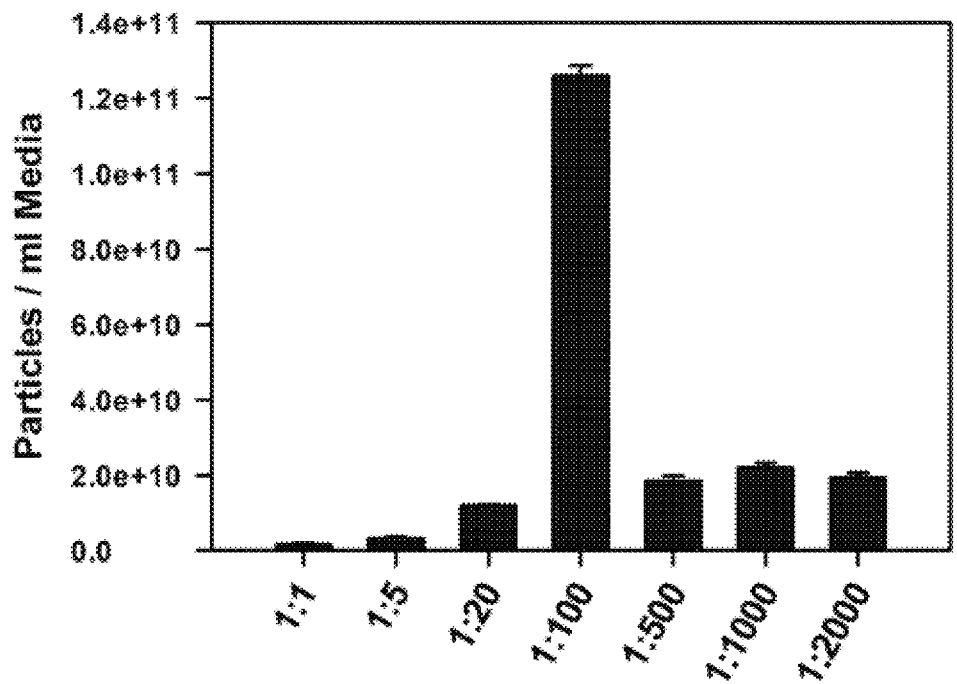
FIG. 1 is a graph showing changes in production amount of stem cell exosomes according to the ratio of TNFα and cycloheximide.
Figure 2:
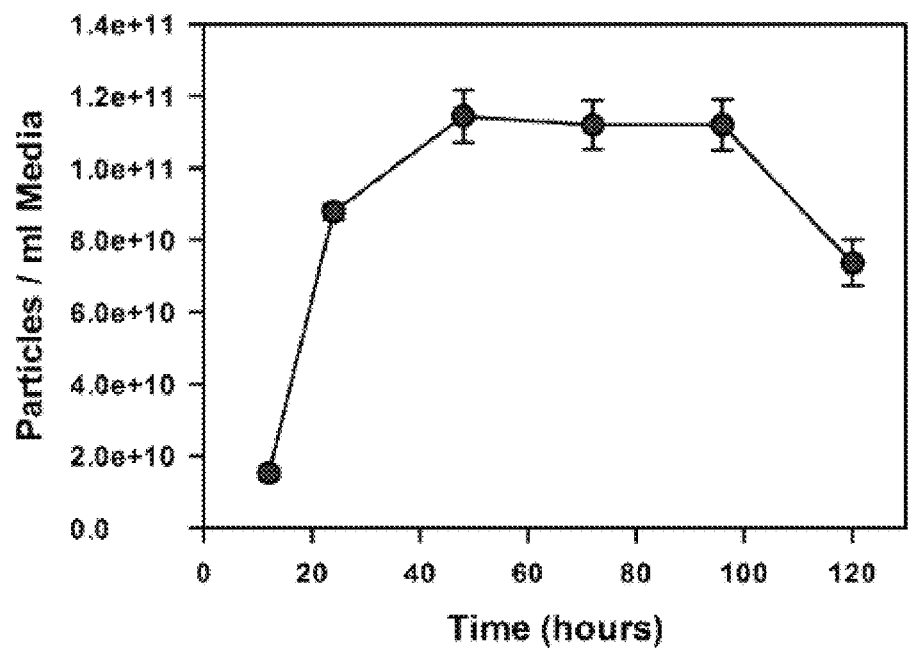
FIG. 2 is a graph showing changes in production amount of exosomes over time in mesenchymal stem cells treated with TNFα and cycloheximide.

Hereinafter, the present application will be described in more detail.

The specific functional descriptions below are only exemplified to describe exemplary embodiments according to the concept of the present application, and the exemplary embodiments according to the concept of the present application may be implemented in various forms and are limited to the exemplary embodiments described in this specification. should not be interpreted.

Since the exemplary embodiments according to the concept of the present application may have various changes and may have various forms, specific exemplary embodiments will be described in detail herein. However, this is not intended to limit the exemplary embodiments according to the concept of the present application to a specific disclosed form, and should be understood to include all modifications, equivalents, and substitutes included in the spirit and scope of the present application.

The terms used in this specification are only used to describe specific exemplary embodiments and are not intended to limit the present application. The singular expression includes the plural expression unless the context clearly dictates otherwise.

Unless otherwise defined, all terms (including technical and scientific terms) used in the present specification may be used as the meaning which may be commonly understood by the person with ordinary skill in the art to which the present application pertains. It will be further understood that terms defined in commonly used dictionaries should not be interpreted in an idealized or excessive sense unless expressly and specifically defined.

An exemplary embodiment of the present application provides a method for preparing mesenchymal stem cell-derived exosomes, the method including: obtaining a cell sample from mesenchymal stem cells; sub-culturing the cell sample in a low-glucose Dulbecco's Modified Eagle's Medium (DMEM) medium; culturing the sub-cultured cells in a substrate medium containing a protein synthesis inhibitory enzyme, and then obtaining a cell culture solution; and isolating exosomes from the cell culture solution.

In the obtaining of the cell sample from mesenchymal stem cells, cells may be obtained by allowing the sample to pass through a membrane to centrifuge a prepared filtrate. In this case, as the membrane, 50 μm to 200 μm nylon may be used, but the membrane is not particularly limited.

As used herein, the term "centrifugation" refers to applying centrifugal force by rotating a material around an axis by an isolation method using a centrifuge. In the present application, the centrifugation may be anyone selected from the group consisting of differential centrifugation, density gradient centrifugation, and gas centrifugation.

As used herein, the term "stem cells" refers to cells having the ability to differentiate into two or more new cells while having a self-replication ability, and may be classified into totipotent stem cells, pluripotent stem cells, and multipotent stem cells. In order to be recognized as the stem cells, cells should continuously replicate in an undifferentiated state, and should be able to differentiate into specific cells under specific culture conditions. The above-described stem cells have recently drawn attention as a candidate for a cell therapeutic agent composition due to their differentiation ability and self-replication ability, and many studies have been conducted. There is an advantage in that it is possible to extract exosomes containing the genetic information, proteins, and growth factors of stem cells therefrom.

The stem cells may be bone marrow stem cells, umbilical cord blood stem cells, or adipose-derived stem cells, may be human-derived or animal-derived or plant-derived stem cells, and may be, for example, human adipose-derived stem cells, but are not limited thereto.

As used herein, the term "exosomes" refers to a small vesicle having a membrane structure secreted from various types of cells, which plays various roles such as delivery of membrane constituents, proteins, and RNAs by binding to other cells and structures.

As used herein, the "DMEM medium" refers to a Dulbecco's Modified Eagle's Medium, and is the most commonly used medium for culturing animal cells. During cell culture, a low-glucose DMEM medium is used, but the DMEM medium is not limited thereto, a high-glucose DMEM medium may also be used, and after cells are grown in the high-glucose medium until reaching 80% to 100% confluency, the cells may be cultured in the low-glucose medium. When cells are cultured in a medium obtained by mixing the high-glucose DMEM and the low-glucose DMEM, there is an advantage in that cells can be rapidly obtained. The concentration of glucose in the low-glucose DMEM may be 800 to 1200 mg/L, and in addition, cells may be cultured by adding fetal bovine serum to the low-glucose DMEM medium, but the culture method is not limited thereto.

As used herein, the term "culture solution" refers to a cell culture supernatant in which mesenchymal stem cells are cultured using a mesenchymal stem cell culture medium. The mesenchymal stem cell culture solution contains various physiologically active materials secreted from cells in a process of culturing mesenchymal stem cells.

The membrane may be 50 μm to 200 μm, but is not particularly limited. Cell pellets may be obtained by centrifugation of a filtrate, which is obtained by allowing the sample to pass through a membrane, at 100 xg to 500 xg for 5 minutes to 30 minutes. Furthermore, the membrane can be used as long as the membrane is a semi-permeable membrane, and may be specifically a nylon membrane filter, but is not particularly limited.

The sub-culturing of the cell pellets may include an antibiotic. The antibiotic may be penicillin and/or streptomycin, but is not limited thereto. The cells may be diluted to a concentration of $1 \times 10^5$ cells/1 ml medium in a 100 to 150 mm cell culture petri dish, and may be cultured in a 3% to 10%, specifically 5% $CO_2$ incubator at a temperature of 30° C. to 40° C., specifically 37° C. Further, cells can be cultured even in a simple shaped bottle without using a petri dish for culturing cells, and cells may be stably maintained for a long period of time, so that there is an advantage in that a large amount of cell culture solution can be produced.

The sub-culturing of the cell pellet sample in a medium may be performed for 4 to 10 passages. There are problems in that when cells are proliferated for 4 or less passages, the degree of expression may be low because cells are not proliferated, and when cells are proliferated for 10 or more passages, cells may be overexpressed.

In the sub-culturing of the cell pellet sample, the DMEM medium may include any one or two or more selected from the group consisting of growth and differentiation factor 11 (GDF11), an epidermal growth factor (EFG), a vascular endothelium growth factor (VEGF), a keratinocyte growth factor (KGF), a hepatocyte growth factor (HGF), transforming growth factor-beta (TGF-b), fibroblast growth factor 2 (FGF-2), an insulin growth factor (IGF), and a platelet-derived growth factor (PDGF).

In the sub-culturing of the cell pellet sample, it is preferred that cells are cultured by replacing the medium every 70 to 75 hours until 80% to 100% confluency. Specifically, it is preferred that cells are cultured by replacing the medium every 72 hours, and when the medium is replaced within 70 hours, there is a problem in that a high purity pellet cannot be obtained, and when the medium is replaced every interval exceeding 75 hours, there is a problem in that a high concentration pellet cannot be obtained. The sub-culturing for extracting high purity mesenchymal stem cell-derived exosomes of the present application has an advantage in that it is possible to enhance the differentiation ability and proliferation ability of exosomes while amplifying mesenchymal stem cells.

The "culture solution" refers to a cell culture supernatant in which mesenchymal stem cells are cultured using a mesenchymal stem cell culture medium. The mesenchymal stem cell culture solution contains various physiologically active materials secreted from cells in a process of culturing mesenchymal stem cells.

The substrate medium may be a serum-free substrate medium or a serum substrate medium. As the substrate medium, a low-glucose DMEM medium is used, but the substrate medium is not limited thereto, and a high-glucose DMEM medium is used, or a medium including both the low-glucose DMEM medium and the high-glucose DMEM medium may be used.

In an exemplary embodiment of the present application, the protein synthesis inhibitory enzyme included in the substrate medium may be any one selected from the group consisting of cycloheximide, anisomycin, aurintricarboxylic acid, diphtheria toxin, edeine, fusidic acid, pactamycin, puromycin, ricin, sodium fluoride, sparsomycin, tetracycline, and *trichoderma*, but is not limited thereto, and can be replaced with any protein biosynthesis inhibitory enzyme capable of the same mechanism. Specifically, it is preferred that the protein synthesis inhibitory enzyme is cycloheximide.

In the obtaining of the cell culture solution of an exemplary embodiment of the present application, the substrate medium may further include TNFα. The TNFα may be included at a concentration of 5 to 500 ng/m L.

In an exemplary embodiment of the present application, the substrate medium may have a TNFα:protein synthesis inhibitory enzyme ratio of 1:10 to 1:2,000. An addition ratio of the TNFα:the protein synthesis inhibitory enzyme may be 1:1 to 1:2,000, specifically 1:10 to 1:1000, and more specifically 1:20 to 1:500, and may be 1:50 to 1:200. When the addition proportion of the protein synthesis inhibitory enzyme is lower than that of TNFα, there is a problem in that the size and amount of exosomes to be extracted may be small, and when the addition ratio of TNFα: the protein synthesis inhibitory enzyme is more than 1:2,000, there is a problem in that the amplification of the cell pellet may be inhibited because the proportion of the protein synthesis inhibitory enzyme is excessive. Specifically, when both TNFα and the protein synthesis inhibitory enzyme are included, there is an advantage in that exosomes can be extracted at high concentration and high purity because the size and number of exosomes to be extracted from stem cells and the content of exosome-derived protein or exosome-derived RNA are increased compared to those when only TNFα is added or only the protein synthesis inhibitory enzyme is added.

In an exemplary embodiment of the present application, a treatment time of the TNFα and/or the protein synthesis inhibitory enzyme may be culturing cells for 30 to 100 hours.

When the treatment time of the TNFα and/or the protein synthesis inhibitory enzyme is less than 30 hours, there is a problem in that the stem cell pellet may not be sufficiently cultured, and when the treatment time is more than 100 hour, there is a problem in that cells may be overexpressed due to an excessively long culturing time.

In an exemplary embodiment of the present application, the isolating of the exosomes may include: obtaining a first supernatant by centrifugation of a collected stem cell culture solution at 200 to 400 xg for 5 to 20 minutes; obtaining a second supernatant by centrifugation of the first supernatant at 1800 to 2300 xg for 5 to 30 minutes; obtaining an exosome pellet by centrifugation or ultracentrifugation of the second supernatant at 90,000 to 110,000 xg for 50 to 100 minutes and removing the supernatant; and suspending the obtained exosome pellet in a PBS buffer and isolating exosome particles. When exosome particles are isolated, the suspension may be treated with ultrasonic waves.

When the exosome pellet is obtained and suspended in the PBS buffer, and then not treated with ultrasonic waves, there is a problem in that high purity exosomes cannot be extracted due to a tightly packed pellet. Therefore, when only exosome particles are isolated from the obtained exosome pellet, there is an advantage in that high purity exosome particles can be extracted.

In an exemplary embodiment of the present application, the obtaining of the cell sample from the mesenchymal stem cells may include making the sample into small sections and treating the small sections for 20 to 40 minutes by adding a collagenase thereto. Then, an enzymatic reaction may be inactivated by adding DMEM thereto, and in this case, it is possible to selectively further include 10% fetal bovine serum (FBS). Moreover, after centrifugation at 200 to 400 xg for 3 to 20 minutes, a cell sample may be obtained by discarding a supernatant, extracting cell pellet particles, and suspending the pellet particles in FBS and Dulbecco's Modified Eagle's Medium (DMEM).

The obtaining of the cell sample may further include re-suspending the obtained cell sample, and then seeding the re-suspended cells. When the seeding of the re-suspended cells is further included, there is an advantage in that it is possible to prevent cell pellet particles from being aggregated in the suspended FBS buffer.

In an exemplary embodiment of the present application, in the obtaining of the sample, the mesenchymal stem cells may be excised from adipose tissue or placental tissue.

Adipose tissue-derived stem cells which may be excised from the adipose tissue mean human adipose-derived stem cells derived from human adipose cells. From this, there is an advantage in that it is possible to extract exosomes containing the genetic information, proteins, and growth factors of adipose cells therefrom.

In an exemplary embodiment of the present application, the stem cell may be an embryonic stem cell, an adult stem cell, or an induced pluripotent stem cell (IPS).

In an exemplary embodiment of the present application, in the cell culture solution, the number of exosomes and a content of any one or more of an exosome-derived protein and exosome-derived RNA may be increased.

In an exemplary embodiment of the present application, $1.1 \times 10^{10}$ or more exosomes per ml of the cell culture solution may be isolated. More specifically, $1.2 \times 10^{12}$ or less exosomes per ml of the cell culture solution may be isolated.

When the exosomes isolated by the method according to an exemplary embodiment of the present application are treated with DNase I, there is an advantage in that purity is increased by 10% or more.

An exemplary embodiment of the present application provides a culture solution include high purity mesenchymal stem cell-derived exosomes prepared using the method.

In an exemplary embodiment of the present application, the culture solution may increase the number of exosomes and a content of any one of an exosome-derived protein and exosome-derived RNA.

In addition, in order to analyze the state of the exosomes, the exosomes may be labeled with a fluorescent material, so that there is an advantage in that an extraction value may be indicated by measuring a fluorescent signal value of exosomes labeled with the fluorescent material to analyze the state of the exosomes.

As used herein, the term "fluorescent material" refers to a material which generates light by a change in physical conditions and chemical treatment. For example, the fluorescent material may be a fluorescent protein such as a green fluorescent protein (GFP), a yellow fluorescent protein (YFP), and a red fluorescent protein (RFP), or may be a photoprotein or a luciferase.

Further, in the exosomes labeled with the fluorescent material, the fluorescent material is located alone in the exosomes, or the exosomes labeled with the fluorescent material may include a fusion protein in which a membrane protein and the fluorescent material are bound. The fusion protein has an advantage in that the amount and signal value of exosomes can be accurately identified because the fluorescent material can bind to the membrane protein directly or through a linker.

An exemplary embodiment of the present application provides a pharmaceutical composition including mesenchymal stem cell-derived exosomes prepared using the method as an active ingredient.

In the pharmaceutical composition of the present application, a generally known and used adjuvant and an additional suitable carrier or diluent may be used. The pharmaceutical composition of the present application may be used in the form of a solid, a solution, an emulsion, a dispersant, a micelle, a liposome, and the like, and a composition obtained herein includes the pharmaceutical composition of the present application as an active ingredient together with an organic or inorganic carrier or excipient suitable for enteral or parenteral application. The active ingredient can be mixed, for example, with the usual non-toxic pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, colloidal silica, potato starch, urea, medium chain length triglycerides, dextran, and other carriers suitable for use in manufacturing preparations, in solid, semisolid, or liquid form. In addition, auxiliary, stabilizing, thickening and coloring agents and flavoring agents may be used.

The pharmaceutical composition may be used by being formulated in the form of an oral formulation such as a powder, a granule, a pill, a capsule, a suspension, an emulsion, a syrup, and an aerosol, an external preparation, a suppository, and a sterile injection solution, according to a typical method. Specifically, when the pharmaceutical composition is prepared, the pharmaceutical composition may be prepared using a commonly used diluent or excipient, such as a filler, an extender, a binder, a wetting agent, a disintegrant, and a surfactant. A solid formulation for oral formulation includes a tablet, a pill, a powder, a granule, a capsule, and the like, and the solid formulation may be prepared by mixing at least one excipient, for example, starch, calcium carbonate, sucrose or lactose, gelatin, and the like with the pharmaceutical composition of the present invention. Further, in addition to simple excipients, lubricants such as magnesium stearate and talc may also be used. A liquid formulation for oral administration corresponds to a suspension, a liquid for internal use, an emulsion, a syrup, and the like, and the liquid formulation may include, in addition to water and liquid paraffin which are simple commonly used diluents, various excipients, for example, a wetting agent, a sweetener, an aromatic, a preservative, and the like. Examples of a formulation for parenteral administration include an aqueous sterile solution, a non-aqueous solvent, a suspension, an emulsion, a freeze-dried preparation, and a suppository. As the non-aqueous solvent and the suspension, it is possible to use propylene glycol, polyethylene glycol, a vegetable oil such as olive oil, an injectable ester such as ethyl oleate, and the like. As a base of the suppository, it is possible to use Witepsol, Macrogol, Tween 61, cacao butter, laurin fat, glycerogelatin, and the like.

The route of administration of the pharmaceutical composition according to the present invention includes, but is not limited to, oral, intravenous, intramuscular, intraarterial, intramedullary, intrathecal, intracardiac, transdermal, subcutaneous, intraperitoneal, intranasal, enteral, topical, sublingual or rectal administration. Oral or parenteral administration is preferred. As used herein, the term "parenteral" includes subcutaneous, intradermal, intravenous, intramuscular, intraarticular, intrasynovial, intrasternal, intrathecal, intralesional and intracranial injection or infusion techniques. The pharmaceutical composition of the present application may also be administered in the form of a suppository for rectal administration.

The pharmaceutical composition of the present application may be administered by any device such that an active material may be transferred to a target cell. A preferred mode of administration and formulation is an injection. The injection may be prepared by using an aqueous solvent such as physiological saline, Ringer's solution, Hank's solution or a sterile aqueous solution, a vegetable oil such as olive oil, a higher fatty acid ester such as ethyl oleate, a non-aqueous solvent such as ethanol, benzyl alcohol, propylene glycol, polyethylene glycol, or glycerin, and the like, and for transmucosal administration, a non-invasive agent publicly known in the art, which is suitable for a barrier through which the injection is to be passed, may be used, and the injection may additionally include a pharmaceutical carrier such as ascorbic acid, sodium hydrogen sulfite, BHA, tocopherol, EDTA, and the like as a stabilizer for preventing degeneration, an emulsifier, a buffering agent for pH control, and a preservative for inhibiting microbial growth, such as phenylmercury nitrate, thimerosal, benzalkonium chloride, phenol, and cresol, benzyl alcohol.

The pharmaceutical composition of the present application may vary depending on various factors including the activity of the specific effective ingredient used, age, body weight, general health, sex, diet, time of administration, route of administration, rate of excretion, drug combination and the severity of a particular disease to be prevented or treated, and the dosage of the pharmaceutical composition varies depending on the condition and body weight of the patient, the degree of disease, the form of drug, the route of administration and duration, but may be appropriately selected by a person skilled in the art, and may be 0.0001 to 50 mg/kg or 0.001 to 50 mg/kg daily. The administration may be carried out once daily, and may be divided into several times. The dosage is not intended to limit the scope of the present invention in any way.

An exemplary embodiment of the present application provides a cosmetic composition including mesenchymal stem cell-derived exosomes prepared using the method as an active ingredient.

The cosmetic composition according to the present application may be any formulation selected from the group consisting of skin lotion, skin softener, skin toner, astringent, lotion, milk lotion, moisturizing lotion, nutrition lotion, massage cream, nourishing cream, moisture cream, hand cream, foundation, essence, nutrition essence, pack, soap, cleansing foam, cleansing lotion, cleansing cream, body lotion, body cleanser, cleanser, treatment, cosmetic solution, cosmetic pack, ointment, gel, liniment, liquid, patch, and spray, but is not limited to a specific formulation, and may have a formulation of a typical cosmetic composition.

Additives are also not limited to each formulation, and general additives in the cosmetic field may be added. Examples of the general additives in the cosmetic field include one or more selected from the group consisting of an antibiotic, a binder, a disintegrant, a diluent, a glidant, a stabilizer, a preservative, a perfume, an oil, water, a surfactant, a moisturizer, a lower alcohol, a thickening agent, a chelating agent, a pigment, and an antiseptic.

Hereinafter, the present invention will be described in detail with reference to Examples and Comparative Examples. However, the following Examples and Comparative Examples are only for illustrating the present invention, and the content of the present invention is not limited by the following Examples.

1. Isolation and Culture of Human Adipose-Derived Mesenchymal Stem Cells

Adipose tissue may be usually obtained by liposuction, but the method is not limited thereto. Human adipose-derived mesenchymal stem cells were isolated from adipose tissue obtained by liposuction as follows:

The isolated adipose tissue was washed with phosphate buffered saline (PBS). After the washed adipose tissue was made into small sections, 0.1% type II collagenase was added thereto. After the tissue was treated at 37° C. for 30 minutes, an enzymatic reaction was inactivated by adding 10% fetal bovine serum (FBS) and low-glucose Dulbecco's Modified Eagle's Medium (DMEM)(10% FBS low-glucose DMEM) thereto, and centrifugation was performed twice at 300 xg for 10 minutes. After the supernatant was discarded and the remaining pellet was suspended in 10% FBS low-glucose DMEM, a pellet was collected by centrifuging the filtrate, which had passed through a 100 um-nylon membrane, at 300 xg for 10 minutes.

Further, after the cell pellet was suspended in a low-glucose DMEM (complete media) including 10% fetal bovine serum (FBS) supplemented with penicillin and streptomycin, the cell pellet was diluted at a concentration of $1 \times 10^5$ cells/1 ml of the medium in a 150-mm cell culture petri dish, and cultured at 37° C. in a 5% $CO_2$ incubator.

The medium was exchanged with a new complete medium every 72 hours, cells were isolated with trypsin-EDTA at the time point when the concentration of cells exceeded 80%, and then sub-cultured at a concentration of $1 \times 10^5$ cells/1 ml of the medium in a new 150-mm cell culture petri dish.

2. Amplification of Mesenchymal Stem Cells

In order to isolate exosomes from the cultured stem cells, differentiation ability and proliferation ability were enhanced by sub-culturing mesenchymal stem cells for 4 to 10 passages while replacing the medium every 72 hours until 80% to 100% confluency in a complete medium supplemented with 5 ng/ml EGF during the sub-culture.

3. Change in Production Amount of Stem Cell Exosomes According to Ratio of TNFα and Cycloheximide Added to Substrate Medium Mesenchymal stem cells of 100% confluency ($5 \times 10^6$ cells), which had been cultured in a 100-mm petri dish, were washed three times with PBS, and the substrate medium was replaced with a low-glucose DMEM. The concentration of exosomes isolated from mesenchymal stem cells treated together with TNFα was measured by NTA by increasing the concentration of cycloheximide while treating the substrate medium with TNFα at a concentration of 50 ng/ml.

At the fixed concentration of 50 ng/ml TNFα, mesenchymal stem cells were treated with a cycloheximide concentration of 50 ng/ml cycloheximide which is a ratio of 1:1, 250 ng/ml cycloheximide which is a ratio of 1:5, 1,000 ng/ml cycloheximide which is a ratio of 1:20, 5,000 ng/ml cycloheximide which is a ratio of 1:100, 25,000 ng/ml cycloheximide which is a ratio of 1:500, 50,000 ng/ml cycloheximide which is a ratio of 1:1000, and 100,000 ng/ml cycloheximide which is a ratio of 1:2000. After the mesenchymal stem cells were cultured for 48 hours, a stem cell culture solution was collected, and then exosomes were purely isolated as follows. A mesenchymal stem cell culture solution was collected, and then centrifuged at 300×g for 10 minutes, and a supernatant was separated, and then the separated supernatant was centrifuged at 2,000 xg for 20 minutes, and then a supernatant was separated. After the separated supernatant was again ultracentrifuged at 100,000×g for 70 minutes, a pellet (exosomes) from which the supernatant had been removed was suspended in PBS and sonicated to isolate exosome particles, and the concentration of isolated exosomes was measured by nanoparticle-tracking analysis (NTA). The results measured by NTA are shown in Table 1.

Referring to the following Table 1, it could be confirmed that $1.58 \times 10^9 \pm 3.2 \times 10^9$ to $1.26 \times 10^{11} \pm 2.8 \times 10^9$ particles per ml of the cell culture solution could be isolated.

TABLE 1

| | TNFα (ng/ml) | Cycloheximide (ng/ml) | Ratio(Cyclo-heximide/TNFα) | Particles/ml Media |
|---|---|---|---|---|
| Example 1 | 50 | 50 | 1 | $1.58 \times 10^9 \pm 3.2 \times 10^8$ |
| Example 2 | 50 | 250 | 5 | $3.2 \times 10^9 \pm 3.6 \times 10^8$ |
| Example 3 | 50 | 1000 | 20 | $1.2 \times 10^{10} \pm 2.2 \times 10^8$ |
| Example 4 | 50 | 5,000 | 100 | $1.26 \times 10^{11} \pm 2.8 \times 10^9$ |
| Example 5 | 50 | 25,000 | 500 | $1.86 \times 10^{10} \pm 1.28 \times 10^9$ |
| Example 6 | 50 | 50,000 | 1000 | $2.2 \times 10^{10} \pm 1.22 \times 10^9$ |
| Example 7 | 50 | 100,000 | 2000 | $1.94 \times 10^{10} \pm 1.18 \times 10^9$ |

4. Isolation of Stem Cell Exosomes According to Treatment Time of TNFα and Cycloheximide Added to Substrate Medium After the substrate medium of Example 3 was treated with TNFα(50 ng/ml) and cycloheximide (5,000 ng/ml), stem cell exosomes were isolated from a culture solution cultured at 37° C. in a 5% $CO_2$ incubator, and the concentration of exosomes was measured by nanoparticle-tracking analysis (NTA), and is shown in Table 2.

Referring to the following Table 2, it could be confirmed that when the substrate medium was treated with TNFα(50 ng/ml) and cycloheximide (5,000 ng/ml) for 30 hours to 100 hours, $1.1 \times 10^{11}$ or more exosomes per ml of the cell culture solution were isolated.

TABLE 2

| | Incubation Time(hours) | Particles/ml Media |
|---|---|---|
| Example 8 | 12 | $1.52 \times 10^{10} \pm 1.28 \times 10^9$ |
| Example 9 | 24 | $8.8 \times 10^{10} \pm 2.08 \times 10^9$ |
| Example 10 | 48 | $1.14 \times 10^{11} \pm 7.3 \times 10^9$ |
| Example 11 | 72 | $1.12 \times 10^{11} \pm 6.8 \times 10^9$ |
| Example 12 | 96 | $1.12 \times 10^{11} \pm 7.04 \times 10^9$ |
| Example 13 | 120 | $7.36 \times 10^{10} \pm 6.4 \times 10^9$ |

5. Isolation of Stem Cell Exosomes According to Type of Additive of Substrate Medium Mesenchymal stem cells of 100% confluency ($1.5 \times 10^7$ cells), which had been cultured in a 150-mm petri dish, were washed three times with PBS. The mesenchymal stem cells cultured in a medium replaced with a low-glucose DMEM were cultured for 48 hours in a medium to which TNFα(50 ng/ml) and cycloheximide (5 ug/ml) were added in combination (Example 14), in a medium to which cycloheximide (5 ug/ml) was added (Example 15), in a medium to which TNFα(50 ng/ml) was added (Comparative Example 1), in a medium to which 1 uM staurosporine was added (Comparative Example 2), in a medium to which 2 uM staurosporine was added (Comparative Example 3), in a medium to which thapsigargin (5 uM) was added (Comparative Example 4), in an amino acid-depleted medium (Hank's balanced salt solution (HBSS))(Comparative Example 5), in a glucose-depleted medium [glucose-depleted media (Gluc(-))](Comparative Example 6), and a substrate medium (10% PBS low-glucose-DMEM)(Comparative Example 7). Then, exosomes were isolated from the culture media by the above-described isolation method.

Figure 3:
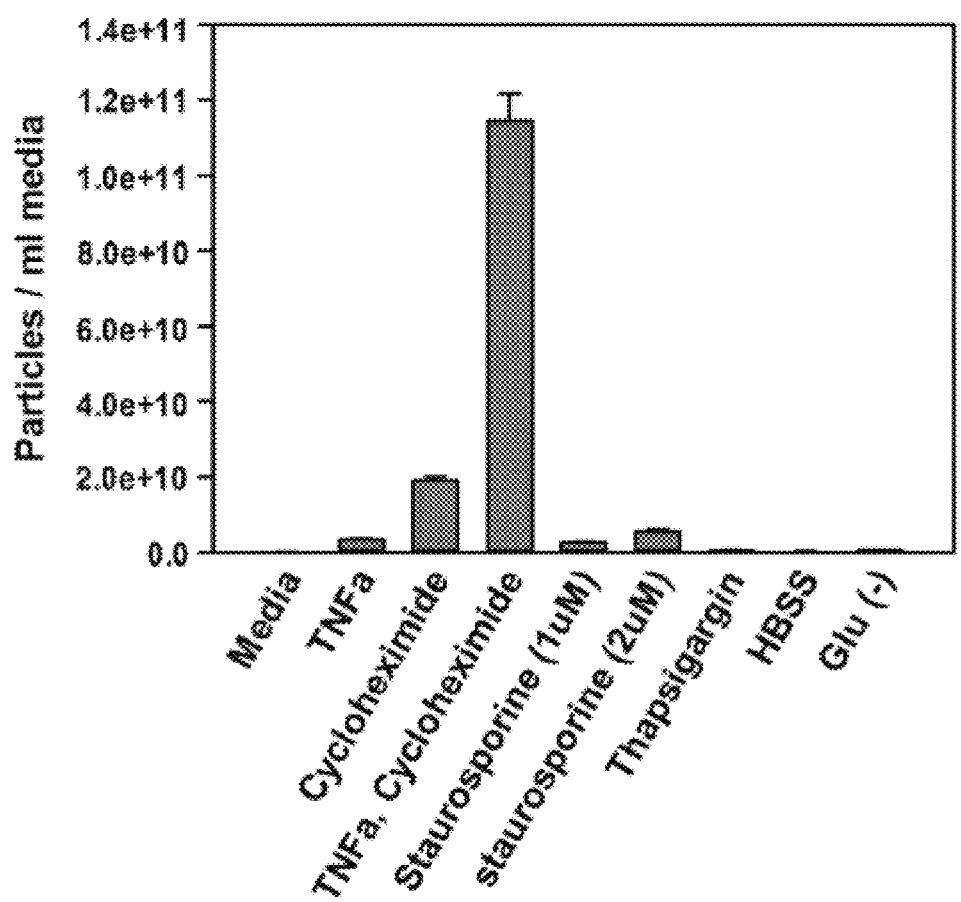
FIG. 3 is a graph showing the concentration of exosomes according to the Examples and Comparative Examples of the present application measured by a nanoparticle-tracking analysis (NTA).
Figure 4:
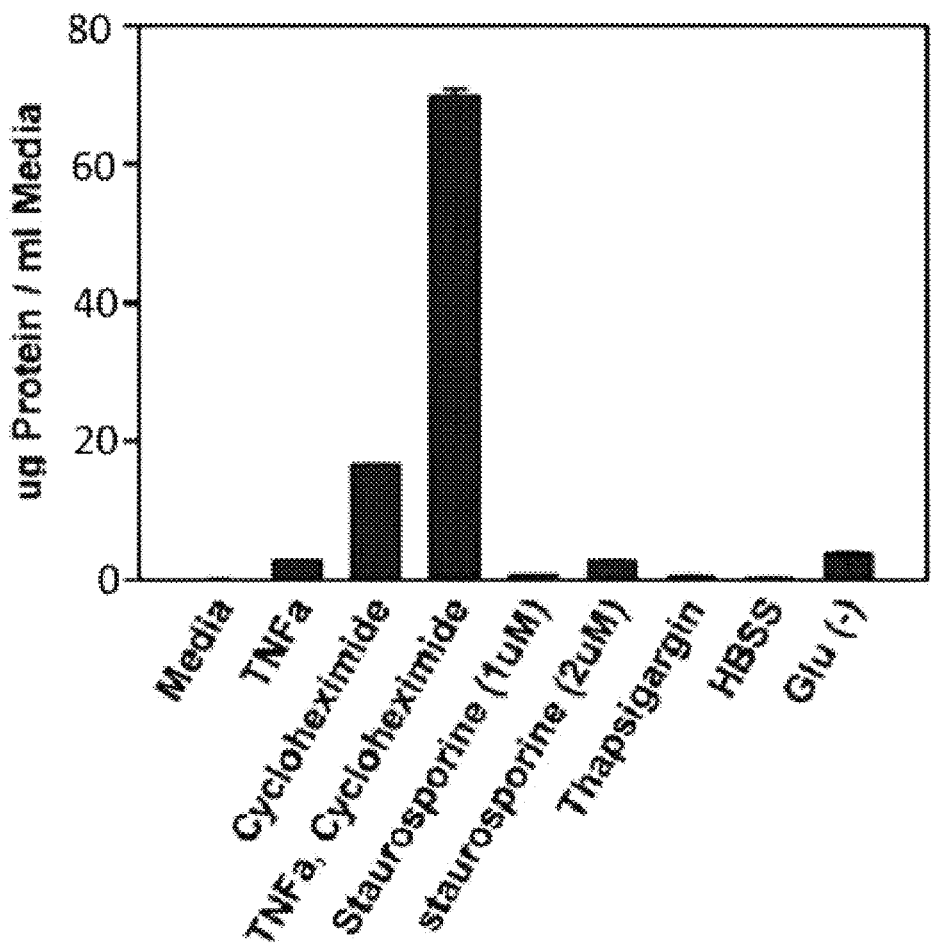
FIG. 4 is a graph showing the concentration of exosomes according to the Examples and Comparative Examples of the present application measured by a Bradford assay.
Figure 5:
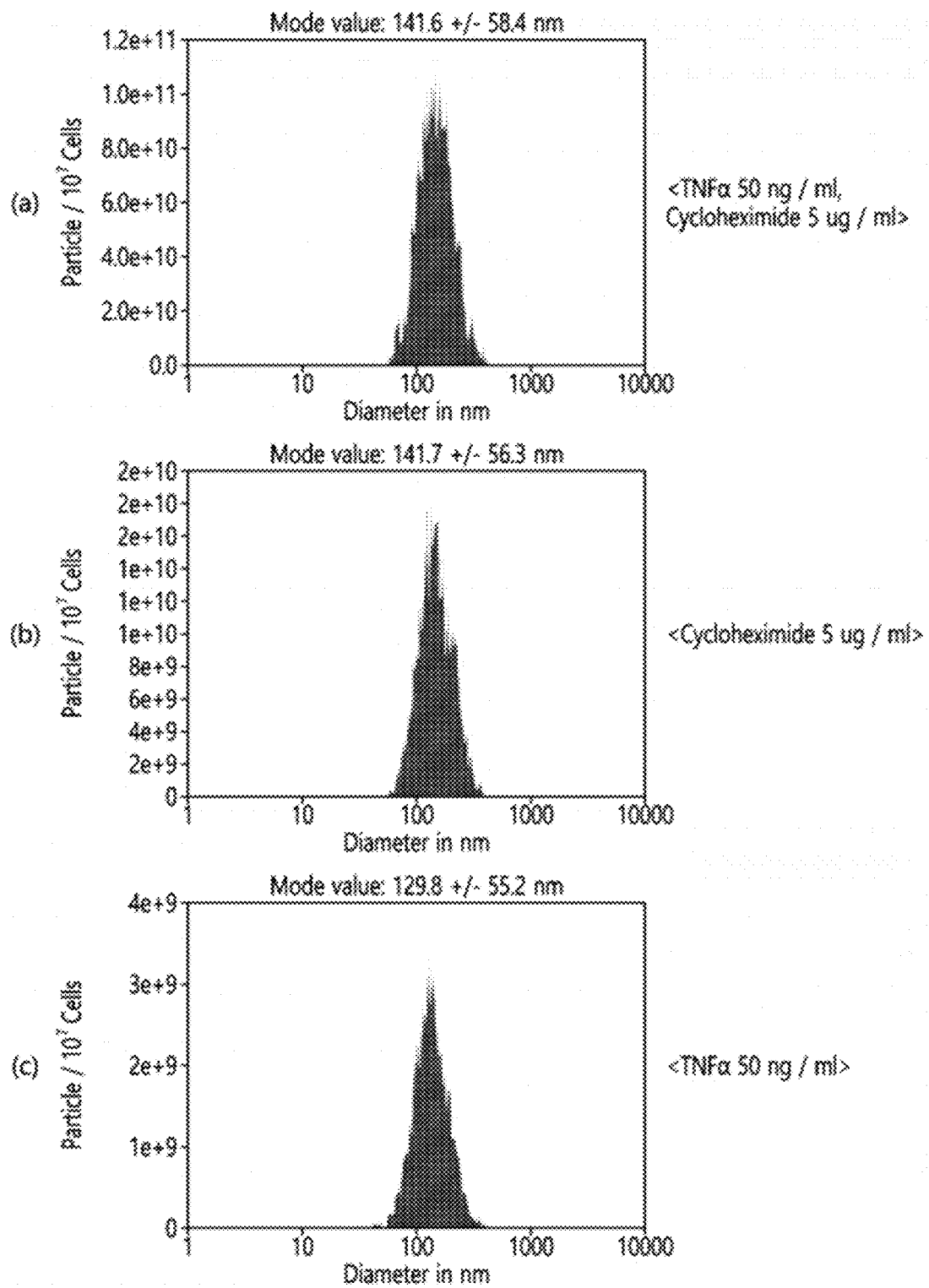
FIG. 5 is a series of graphs showing the size of exosomes and the particle distribution histogram according to the size of exosomes, of Example 14 (a), Example 15 (b), and Comparative Example 1 (c) for the Examples and Comparative Examples of the present application, which are measured by NTA.
Figure 6:
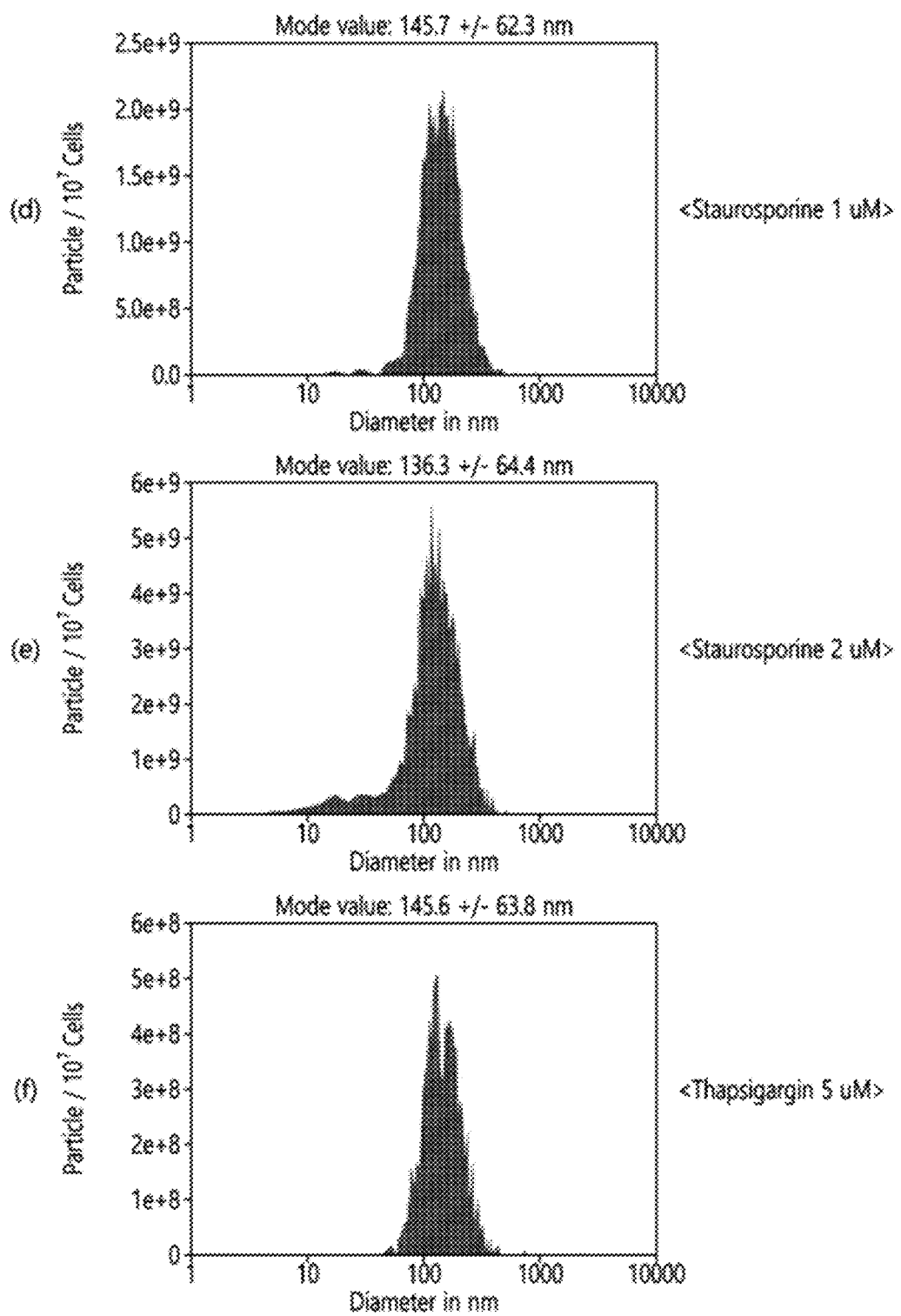
FIG. 6 is a series of graphs showing the size of exosomes and the particle distribution histogram according to the size of exosomes, of Comparative Example 2 (d), Comparative Example 3 (e), and Comparative Example 4 (f) for the Examples and Comparative Examples of the present application, which are measured by NTA.
Figure 7:
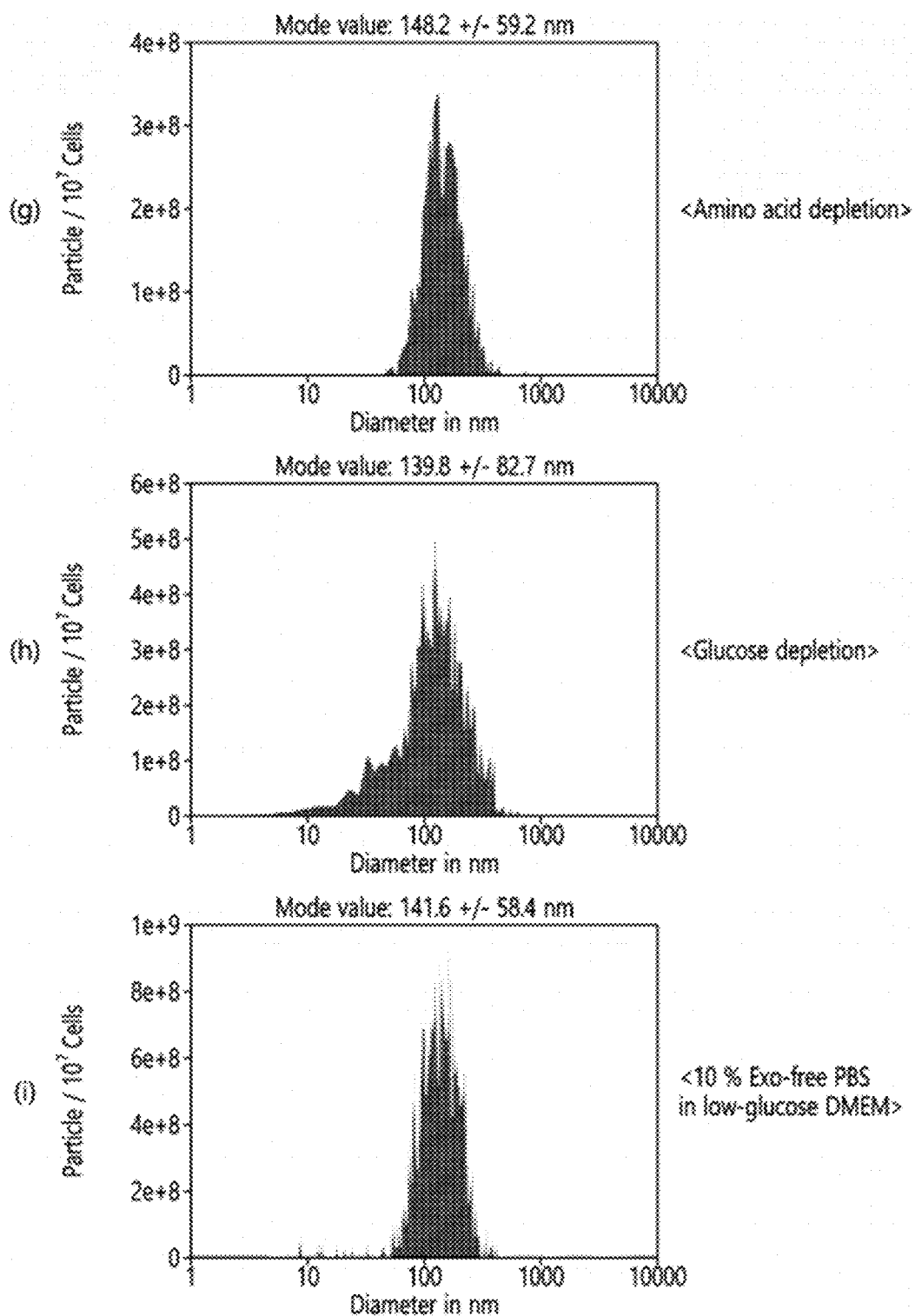
FIG. 7 is a series of graphs showing the size of exosomes and the particle distribution histogram according to the size, of exosomes of Comparative Example 5 (g), Comparative Example 6 (h), and Comparative Example 7 (i) for the Examples and Comparative Examples of the present application, which are measured by NTA.
Figure 8:
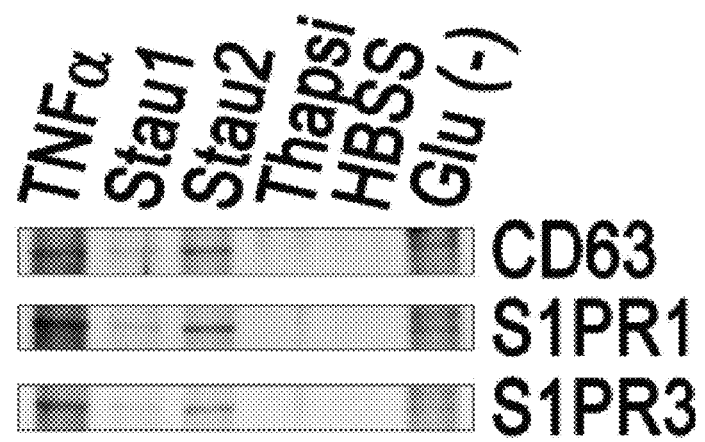
FIG. 8 illustrates the western blot of exosomes according to the Examples and Comparative Examples of the present application.

For the isolated exosomes, the number of particles and the size of particles were quantified by nanoparticle-tracking analysis (NTA), and proteins were quantified by Bradford assay. Furthermore, an exosome marker was measured using western blotting. The number of particles of the isolated exosomes is illustrated in FIGS. 3 and 4, and shown in the following Table 3. The amount of proteins and the particle size of the exosomes are shown in FIGS. 5 to 7 and Table 4. Further, the expression of exosome markers CD63, sphingosine-1-phosphate receptor 1 (S1PR1), and sphingosine-1-phosphate receptor 3 (S1PR3) is illustrated in FIG. 8.

Figure 9:
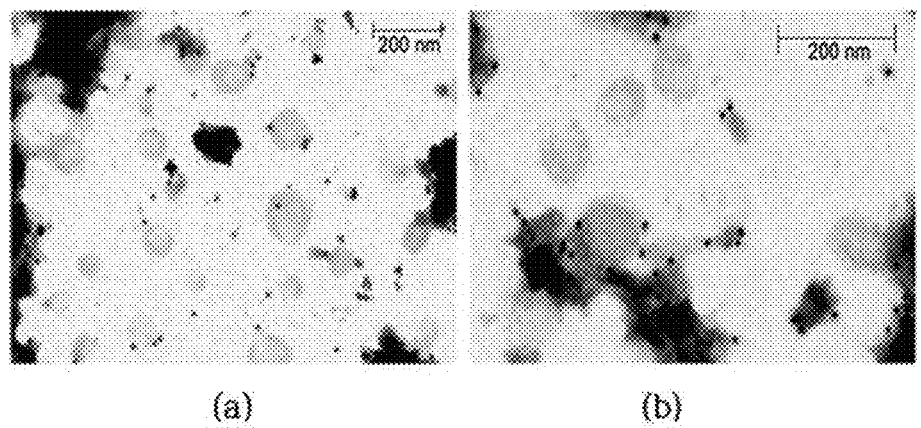
FIG. 9 illustrates the exosomes of the present application by transmission microscopy (TEM) photographs.
Figure 10:
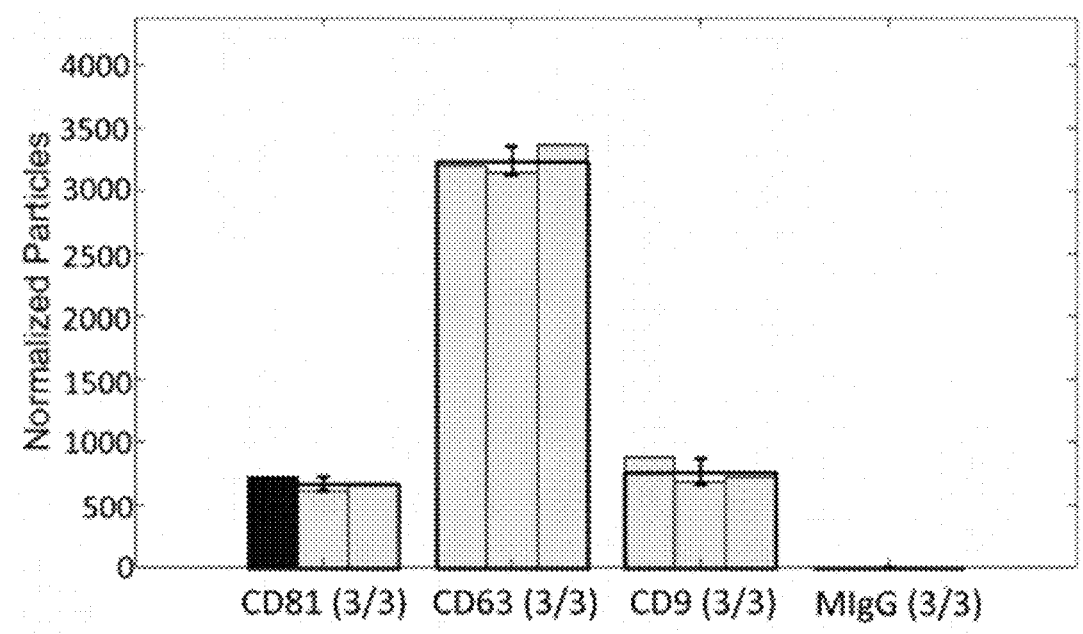
FIG. 10 illustrates a graph for analyzing the exosomes of the present application by an Exoview technique.

Particles of the size of mode value 141.6±58.4 nm were induced from mesenchymal stem cells under conditions of treatment with TNFα(50 ng/ml) and cycloheximide (5 ug/ml) of Example 14, and are shown in Table 4 and FIG. 5A. Referring to FIG. 9, exosome particles were surrounded by a bilipid membrane, and the expression of CD63, which is a marker for exosomes, was confirmed by transmission electron microscopy (TEM). Referring to FIG. 10, in a test of surface marker expression of exosomes using Exoview, mesenchymal stem cell-derived exosomes exhibited exosome markers of a cluster of differentiation 63 (CD63), a cluster of differentiation 9 (CD9), and a cluster of differentiation 81 (CD81).

TABLE 3

| | Conditions | Particles/ml Media | Particles/$10^7$ Cells |
|---|---|---|---|
| Example 14 | TNFα(50 ng/ml), Cycloheximide(5 ug/ml) | $1.144 \times 10^{11} \pm 7.304 \times 10^9$ | $2.288 \times 10^{12} \pm 1.461 \times 10^{11}$ |
| Example 15 | Cycloheximide(5 ug/ml) | $1.900 \times 10^{10} \pm 1.140 \times 10^9$ | $3.800 \times 10^{11} \pm 2.280 \times 10^{10}$ |
| Comparative Example 1 | TNFα(50 ng/ml) | $3.400 \times 10^8 \pm 1.740 \times 10^7$ | $6.800 \times 10^{10} \pm 3.480 \times 10^9$ |
| Comparative Example 2 | Staurosporine(1 uM) | $2.450 \times 10^9 \pm 2.650 \times 10^8$ | $4.900 \times 10^{10} \pm 5.300 \times 10^9$ |
| Comparative Example 3 | Staurosporine(2 uM) | $5.500 \times 10^9 \pm 7.000 \times 10^8$ | $1.100 \times 10^{11} \pm 1.400 \times 10^{10}$ |
| Comparative Example 4 | Thapsigargin(5 uM) | $5.000 \times 10^8 \pm 1.050 \times 10^8$ | $1.000 \times 10^{10} \pm 2.100 \times 10^9$ |
| Comparative Example 5 | HBSS | $3.350 \times 10^8 \pm 4.800 \times 10^7$ | $6.700 \times 10^9 \pm 9.600 \times 10^8$ |
| Comparative Example 6 | Gluc(-) | $5.500 \times 10^8 \pm 4.750 \times 10^7$ | $1.100 \times 10^{10} \pm 9.500 \times 10^8$ |
| Comparative Example 7 | 10% PBS low-glucose-DMEM | $1.200 \times 10^8 \pm 1.040 \times 10^7$ | $2..400 \times 10^9 \pm 2.080 \times 10^8$ |

TABLE 4

| | Conditions | μg Protein/ml Media | Size in diameter(mode value ± SD) |
|---|---|---|---|
| Example 14 | TNFα(50 ng/ml), Cycloheximide(5 ug/ml) | 69.847 ± 0.841 | 141.6 ± 58.4 |
| Example 15 | Cycloheximide(5 ug/ml) | 16.667 ± 0.135 | 141.7 ± 56.3 |
| Comparative Example 1 | TNFα(50 ng/ml) | 2.982 ± 0.024 | 129.8 ± 55.2 |
| Comparative Example 2 | Staurosporine(1 uM) | 0.780 ± 0.025 | 145.7 ± 62.3 |
| Comparative Example 3 | Staurosporine(2 uM) | 2.950 ± 0.050 | 136.3 ± 64.4 |
| Comparative Example 4 | Thapsigargin(5 uM) | 0.600 ± 0.025 | 145.6 ± 63.8 |
| Comparative Example 5 | HBSS | 0.291 ± 0.025 | 148.2 ± 59.2 |
| Comparative Example 6 | Gluc(-) | 3.630 ± 0.125 | 139.8 ± 82.7 |
| Comparative Example 7 | 10% PBS low-glucose-DMEM | 0.105 ± 0.006 | 141.6 ± 58.4 |

It is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method for preparing mesenchymal stem cell-derived exosomes, the method comprising: obtaining a cell sample from mesenchymal stem cells;
   sub-culturing the cell sample in a low-glucose Dulbecco's Modified Eagle's Medium (DMEM) medium;
   culturing the sub-cultured cells in a substrate medium containing a protein synthesis enzyme inhibitor, and then obtaining a cell culture solution; and
   isolating exosomes from the cell culture solution,
   wherein in the obtaining of the cell culture solution, the substrate medium further comprises TNFα,
   wherein the protein synthesis enzyme inhibitor is any one or more selected from the group consisting of cycloheximide, anisomycin, aurintricarboxylic acid, diphtheria toxin, edeine, fusidic acid, pactamycin, puromycin, ricin, sodium fluoride, sparsomycin, tetracycline, and *Trichoderma*, and
   wherein the substrate medium has a TNFα: protein synthesis inhibitory enzyme ratio of 1:10 to 1:2000.

2. The method of claim 1, wherein TNFα is comprised at a concentration of 5 to 500 ng/m L.

3. The method of claim 1, wherein a treatment time of the TNFα and the protein synthesis enzyme inhibitor is 30 to 100 hours.

4. The method of claim 1, wherein in the cell culture solution,
   the number of exosomes and a content of any one or more of an exosome-derived protein and exosome-derived RNA are increased.

5. The method of claim 1, wherein $1.1 \times 10^{11}$ or more exosomes per ml of the cell culture solution are isolated.

6. The method of claim 1, wherein in the sub-culturing of the cell sample,
   the medium comprises one or more selected from the group consisting of EGF, FGF-2, GDF11, KGF, HGF, PDGF, VEGF, IGF, and TGF-b, and the sub-culturing of the cell sample is performed for 4 to 10 passages.

7. The method of claim 1, wherein the exosome is one or more marker selected from the group consisting of CD63, CD9, CD81, S1PR1, and S1PR3.

8. The method of claim 1, wherein in the obtaining of the sample, the mesenchymal stem cells are obtained from adipose tissue or placental tissue.

9. The method of claim 8, wherein the stem cell is an embryonic stem cell, an adult stem cell, or an induced pluripotent stem cell (IPS).

\* \* \* \* \*